(12) United States Patent
Schuelke et al.

(10) Patent No.: US 11,000,282 B2
(45) Date of Patent: May 11, 2021

(54) PUNCHING DEVICE AND METHOD FOR PUNCHING A LUMEN AND IMPLANTING AN IMPLANT DEVICE

(71) Applicant: Kardion GmbH, Stuttgart (DE)

(72) Inventors: Armin Schuelke, Aidlingen (DE); Hardy Baumbach, Stuttgart (DE); Inga Schellenberg, Stuttgart (DE); Tobias Bergem, Korntal-Münchingen (DE)

(73) Assignee: KARDION GMBH, Stuttgart (DE)

( * ) Notice: Subject to any disclaimer, the term of this patent is extended or adjusted under 35 U.S.C. 154(b) by 507 days.

(21) Appl. No.: 15/613,409

(22) Filed: Jun. 5, 2017

(65) Prior Publication Data

US 2017/0348005 A1 Dec. 7, 2017

(30) Foreign Application Priority Data

Jun. 6, 2016 (DE) ..................... 10 2016 209 871.3

(51) Int. Cl.
*A61B 17/11* (2006.01)
*A61B 17/3205* (2006.01)
*A61M 39/00* (2006.01)
*A61B 17/12* (2006.01)
*A61B 17/32* (2006.01)
*A61B 17/34* (2006.01)
*A61B 17/00* (2006.01)

(52) U.S. Cl.
CPC ........ *A61B 17/11* (2013.01); *A61B 17/12045* (2013.01); *A61B 17/32002* (2013.01); *A61B 17/32053* (2013.01); *A61M 39/00* (2013.01); *A61B 17/12036* (2013.01); *A61B 2017/00654* (2013.01); *A61B 2017/00659* (2013.01); *A61B 2017/1107* (2013.01); *A61B 2017/1135* (2013.01); *A61B 2017/320064* (2013.01); *A61B 2017/3454* (2013.01)

(58) Field of Classification Search
CPC .............. A61B 17/11; A61B 17/32053; A61B 17/3209; A61B 17/32096; A61B 2017/1135; A61B 2017/1107; A61B 2017/1114; A61B 17/3423; A61B 2017/3425; A61B 2017/3427; A61F 2/95; A61F 2/966; A61F 2002/9517; A61F 11/002

See application file for complete search history.

(56) References Cited

U.S. PATENT DOCUMENTS

| | | | | |
|---|---|---|---|---|
| 3,645,268 A | * | 2/1972 | Capote | A61F 11/002 604/117 |
| 6,471,713 B1 | * | 10/2002 | Vargas | A61B 17/11 606/153 |
| 6,979,338 B1 | * | 12/2005 | Loshakove | A61B 17/064 606/149 |
| 2003/0040765 A1 | | 2/2003 | Breznock | |
| 2006/0190036 A1 | * | 8/2006 | Wendel | A61B 17/0057 606/213 |

(Continued)

*Primary Examiner* — Shaun L David
*Assistant Examiner* — Christian D Knauss
(74) *Attorney, Agent, or Firm* — Knobbe Martens Olson & Bear, LLP

(57) ABSTRACT

A punching device for punching a lumen and implanting an implant device includes at least the implant device for punching the lumen and for implantation into the lumen. In addition, the punching device includes an implantation device, a closure device, and an actuation device.

13 Claims, 5 Drawing Sheets

(56) References Cited

U.S. PATENT DOCUMENTS

| | | |
|---|---|---|
| 2011/0137394 A1 | 6/2011 | Lunsford et al. |
| 2014/0012282 A1* | 1/2014 | Fritsch .................. A61F 11/002 606/109 |
| 2016/0067395 A1 | 3/2016 | Jimenez et al. |

* cited by examiner

PUNCHING DEVICE AND METHOD FOR PUNCHING A LUMEN AND IMPLANTING AN IMPLANT DEVICE

This application claims priority under 35 U.S.C. § 119 to patent application no. DE 10 2016 209 871.3, filed Jun. 6, 2016 in Germany; the disclosure of which is incorporated herein by reference in its entirety.

BACKGROUND

The approach is directed to a device or a method of the type described in the disclosure.

In order to open a liquid- and/or air-filled lumen, which is in the form of a blood vessel in this case, by way of example, but which can also be a stomach, an intestine, or a trachea, it is possible to manually cut into the blood vessel using a scalpel. A piece of the blood vessel can then be removed in various ways. The blood vessel can also be merely expanded and subsequently sutured together again. When the blood vessel is punched, it is necessary to at least partially clamp the blood vessel and/or connect the patient to a heart-lung machine. In order to make it possible, for example, to route a power cable, which is connected to a VAD pump, out of the aorta, it would be necessary to punch the ascending aorta and subsequently implant a wire mesh into the aorta in order to hold the aorta open.

SUMMARY

Against this background, the approach presented here provides a punching device for punching a lumen and implanting an implant device, and a method for punching a lumen and implanting an implant device according to the disclosure. Due to the measures described in the dependent claims, advantageous refinements and improvements of the punching device described in the disclosure are possible.

A punching device for punching a lumen and implanting an implant device is provided. In this case, the lumen can be, for example, a blood vessel, a stomach, an intestine, or a trachea. The punching device comprises at least the implant device, an implantation device, a closure device, and an actuation device. The implant device is designed for punching the lumen and for being implanted into the lumen. The implantation device is coupled to the implant device and is designed for punching the implant device into the lumen by way of a forward motion and for effectuating the implantation of the implant device into the punched lumen by way of a return motion of at least one part of the implantation device. The closure device is coupled at least to the implantation device and is designed in such a way that, in an open state, it releases a restoring force for effectuating the forward motion of the implantation device, in order to punch the lumen. In a closed state, the closure device can be designed for holding the implantation device, including the coupled implant device, in the punching device. The actuation device is coupled to the closure device and is designed for bringing about the opened state of the closure device and effectuating the return motion of the implantation device in response to at least one actuation. The actuation device can also be designed for bringing about the opened state of the closure device in response to a first actuation and for effectuating the return motion of the implantation device in response to a second actuation.

A punching device presented here makes it possible to punch a lumen and implant an implantation device by actuating a single actuation device. The actuations can be effectuated, for example, by a surgeon by moving a single operating element, for example in the form of a rotary knob or a push-button. The operating element can be part of the actuation device or can be coupled to the actuation device. In this case, the implant device advantageously performs the function of the punch and of the implant. Therefore, an additional punching device for punching the lumen is not necessary. In this way, by means of the above-described forward motion of the implantation device, the lumen is punched by the implant device and the implant device is already positioned at the point in the lumen where it is to be implanted. In order to perform the implantation, all that is necessary is to then withdraw the implantation device. The punching device presented here can punch the lumen and implant the implant device in only two simple motions, namely the forward motion and the return motion of the implantation device. The punching device can comprise a housing which accommodates the implant device, the implantation device, the closure device, and the actuation device. The closure device can be designed as a plug-and-socket connector which can comprise a spring for providing the restoring force or can be coupled to such a spring. The plug-and-socket connector and/or the spring can be preloaded, or can have been already preloaded, during the assembly of the punching device. According to one embodiment, the punching device has a size and a shape which make it possible for a surgeon to handle the punching device. For example, the punching device has a length of less than 30 cm and has a width or height of less than 10 cm. According to one embodiment, the punching device is designed as a device for single use.

For the purpose of guiding and surrounding the implant device, the implantation device can comprise at least one inner sleeve for guiding the implant device and an outer sleeve for surrounding the implant device, wherein the outer sleeve can be designed for surrounding the inner sleeve in an at least partially linearly movable manner. In this way, the inner sleeve and the outer sleeve can be movable separately from each other. When the outer sleeve is designed for carrying out the return motion in order to effectuate the implantation of the implant device into the punched lumen, the inner sleeve can be designed, for example, to stand still during the return motion of the outer sleeve. In this way, the implant device can be held by the inner sleeve at the intended point in the lumen, while the return motion of the outer sleeve effectuates the implantation at this point.

This can be possible, for example, when the implant device comprises a mesh having shape memory. The mesh having shape memory can be, for example, a wire mesh in this case, which is made at least partially of a shape memory alloy. The mesh having shape memory can be disposed, for example, in such a way that it is compressed by the surrounding outer sleeve and can expand to a predetermined size during implantation in the lumen, in order to ensure a rapidly sealing connection between the lumen and the implant device.

The implant device can also be designed as a wire mesh which is multifunctional and, for example, comprises a sealing element. For example, the implant device consists of a wire mesh, on the one hand and, on the other hand, is encapsulated in a sealing material, for example. Additionally or alternatively, the implant device can be designed in such a way that, in the implanted state, it holds the blood vessel open.

It is also advantageous when the punching device comprises an opening device which is coupled to the implantation device, wherein the opening device can comprise at least one opening unit which can be designed for opening the lumen before the punching, in response to the forward motion. This opening unit can be designed, for example, as a pointed tip which punctures the lumen, in a punctiform and, therefore, gentle manner, before the punching. When the opening unit also comprises a barb, a lumen section of the lumen, which is to be punched out, can be advantageously captively fixed on the barb during the opening of the lumen. When the opening device also executes a return motion in response to the return motion of the implantation device, the punched lumen section can be advantageously reliably removed from the lumen.

In order to save installation space, it is possible according to one embodiment to dispose the implant device and the implantation device ideally on one axis. The opening device can be accommodated, in this case, at least partially by the implantation device and/or the implant device in order to also allow for opening on the same axis of motion.

According to one embodiment, the closure device can comprise at least one bayonet lock including a rotatable rotary element and a rotatable and linearly movable linear unit, wherein, in order to provide the restoring force, the closure device can comprise at least one spring which can be loaded in a closed state of the bayonet lock. A plug-and-socket connector such as a bayonet lock can be reliably closed and easily mechanically opened. For this purpose, the bayonet lock can be advantageously designed to be transferred from the closed state into the opened state by means of a rotation of the rotary element, wherein the linear unit can be designed in such a way that, when the bayonet lock is transferred into the opened state, the linear unit executes a linear opening motion in the direction of an outlet opening of the punching device in order to effectuate the forward motion of the implantation device coupled to the linear unit. When the implantation device, together with the implant device, is coupled to the linear unit, the implantation device and the implant device can therefore execute the forward motion in response to the linear opening motion of the linear unit.

The outlet opening is an opening in the housing of the punching device, through which the implant device and the implantation device at least partially emerge from the housing during punching and implantation.

In order to couple the implantation device to the closure device, at least one sleeve of the implantation device can comprise at least one pin to be accommodated in at least one guide groove of the linear unit and/or the linear unit comprises at least the guide groove for accommodating the pin of the sleeve. The guide groove and the pin can be designed in such a way in this case that, in a coupled state, they effectuate the return motion of the implantation device in response to the actuation of the actuation device after the lumen has been punched. It is advantageous, in particular, when the inner sleeve and the outer sleeve each comprise such a pin, which are accommodated in different guide grooves in the linear unit. By way of a different embodiment of the guide grooves, the inner sleeve and the outer sleeve can be guidable in the guide grooves in different ways and, therefore can be moved in different ways. The opening device can also comprise such a pin which can be accommodated in one further groove in the linear unit in order to make the opening device movable, for example, in response to the forward motion of the linear unit.

According to one embodiment, the punching device can comprise a rotary knob or a push-button which is designed for effectuating the at least one actuation of the actuation device in response to a rotary actuation or a push actuation. Advantageously, the opened state of the closure device can be brought about first, for example, by continuing the rotary actuation and, subsequent thereto, the return motion of the implantation device can be executed. For this purpose, the linear unit can be designed to be rotatable in order to be able to continue the rotary actuation of the rotary knob. In this way, the lumen can be punched and the implant device can be implanted by means of the punching device simply by way of a rotary actuation or a push actuation. The rotary or push actuation can take place in this case by means of an operator of the punching device, for example, by a surgeon or an operating surgeon.

A method for punching a lumen and implanting an implant device comprises at least the following steps:

bringing about an opened state of a closure device in order to release a restoring force for effectuating a forward motion of an implantation device coupled to the closure device, in order to punch the lumen by means of the implant device coupled to the implantation device, wherein the opened state of the closure device is brought about by means of at least one actuation of an actuation device coupled to the closure device; and executing a return motion of the implantation device in order to effectuate the implantation of the implant device, which is coupled to the implantation device, into the punched lumen, wherein the return motion of the implantation device is executed by means of the at least one actuation of the actuation device.

This method can be carried out using the aforementioned punching device. The above-described advantages of the punching device can also be implemented by means of such a method.

BRIEF DESCRIPTION OF THE DRAWINGS

Exemplary embodiments of the approach presented here are represented in the drawings and are described in greater detail in the following description. In the drawings.

DETAILED DESCRIPTION

Figure 1:
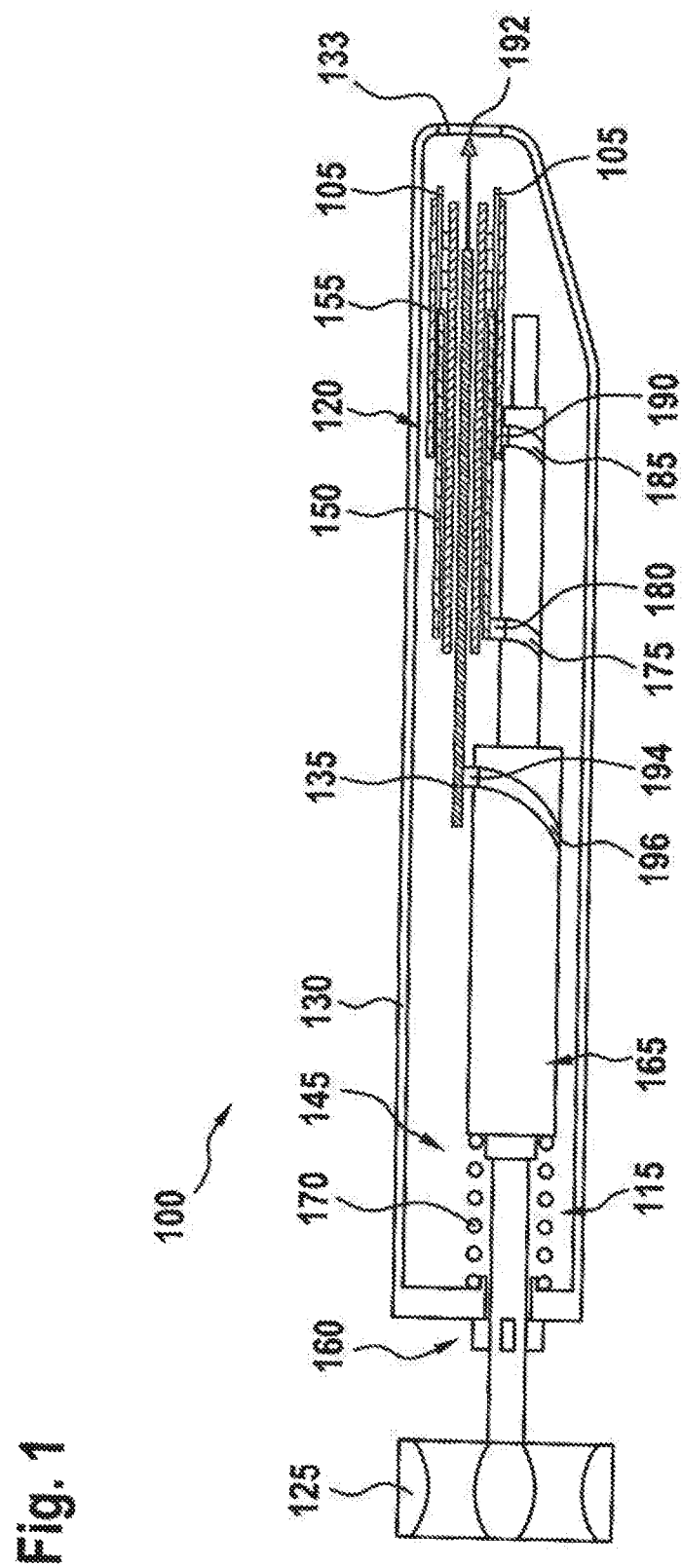
FIG. 1 shows a cross-section of a side view of a punching device for punching a lumen and implanting an implant device according to one exemplary embodiment.

In the following description of favorable exemplary embodiments of the present approach, the same or similar reference characters are used for the elements that are represented in the various figures and act in a similar manner, wherein a description of these elements is not repeated.

FIG. 1 shows a cross-section of a side view of a punching device 100 for punching a lumen and implanting an implant device 105 according to one exemplary embodiment. According to this exemplary embodiment, the lumen is in the form of a blood vessel. According to one alternative exemplary embodiment, the lumen can also be a stomach, an intestine, or a trachea.

The punching device 100 comprises the implant device 105, a closure device 115, an implantation device 120, and an actuation device 125.

Optionally, the punching device 100 also comprises a housing 130, in which the aforementioned devices 105, 115, 120, except for the actuation device 125, are accommodated for protection. The housing 130 comprises, at one end of the punching device 100, an outlet opening 133, through which the implant device 105 and the implantation device 120 at least partially emerge from the punching device 100 during punching. Optionally, the punching device 100 also comprises an opening device 135 for opening the blood vessel before the punching.

The implant device 105 is designed for punching the blood vessel and, according to this exemplary embodiment, also for holding the blood vessel open in a state in which the implant device has been implanted into the blood vessel. For this purpose, the implant device 105 according to this exemplary embodiment comprises a wire mesh having shape memory, whereby the implant device 105 is designed to sealingly expand in the blood vessel when the implant device is in the implanted state.

The implantation device 120 is coupled to the implant device 105 and is designed for punching the implant device 105 into the blood vessel by way of a forward motion and for effectuating the implantation of the implant device 105 into the punched blood vessel by way of a return motion of at least one part of the implantation device 120.

The closure device 115 is coupled to the implantation device 120 and is designed in such a way that, in an open state, it releases a restoring force for effectuating the forward motion of the implantation device 120, in order to punch the blood vessel. According to this exemplary embodiment, the closure device 115 is in a closed state 145 in which the closure device 115 is designed for holding the implantation device 120, including the coupled implant device 105, in the housing 130 of the punching device 100.

The actuation device 125 is coupled to the closure device 115 and is designed for bringing about the opened state of the closure device 115 in response to a first actuation and effectuating the return motion of the implantation device 120 in response to a second actuation. According to one alternative exemplary embodiment, the forward motion, the opened state, and the linear motion can also be executed/brought about in response to a single actuation of the actuation device 125. According to this exemplary embodiment, the actuation device 125 is designed as a rotary knob which is designed for effectuating, in response to a rotary actuation, the first actuation of the actuation device 125 and then the second actuation of the actuation device. According to one alternative exemplary embodiment, the actuation device 125 comprises, in addition or as an alternative to the rotary knob, a push-button which is designed for effectuating the above-described actuations of the actuation device 125 in response to a push actuation.

According to this exemplary embodiment, the implantation device 120 comprises an inner sleeve 150 and an outer sleeve 155. The inner sleeve 150 is partially accommodated by the outer sleeve 155, wherein the outer sleeve 155 surrounds the inner sleeve 150 in a linearly movable manner. The inner sleeve 150 is designed for guiding the implant, device 105. The outer sleeve 155 is designed for surrounding the implant device 105 and holding it in a compressed state before the return motion is executed; for this purpose, the implant device 105 according to this exemplary embodiment is completely accommodated in the outer sleeve 155. According to this exemplary embodiment, the implant device 105 and the implantation device 120 are disposed on one axis.

According to this exemplary embodiment, the outer sleeve 155 is designed for executing the return motion for effectuating the implantation of the implant device 105 into the punched blood vessel, while the inner sleeve 150 stands still. According to this exemplary embodiment, the inner sleeve 150 is designed for executing a return motion out of the blood vessel in response to a third actuation of the actuation device 125, after the implant device 105 has been implanted by means of the return motion of the outer sleeve 155.

According to this exemplary embodiment, the closure device 115 is designed as a plug-and-socket connector in the form of a bayonet lock which comprises a rotatable rotary element 160 and a rotatable and linearly movable linear unit 165. According to this exemplary embodiment, the linear unit 165 is coupled to the implantation device 120 and is rotatable in response to the actuation. In order to provide the restoring force, the closure device 115 according to this exemplary embodiment comprises a spring 170 which is loaded in the closed state 145 of the bayonet lock. The bayonet lock is designed to be transferred from the closed state 145 into the opened state by means of a rotation of the rotary element 160, wherein the linear unit 165 is designed in such a way that, when the bayonet lock is transferred into the opened state, the linear unit executes a linear opening motion in the direction of the outlet opening 133 of the punching device 100 in order to effectuate the forward motion of the implantation device 120 coupled to the linear unit 165.

For the purpose of coupling the closure device 115 to the implantation device 120, the linear unit 165 according to this exemplary embodiment comprises an inner sleeve groove 175 for accommodating an inner sleeve cam 180 of the inner sleeve 150 and an outer sleeve groove 185 for accommodating an outer sleeve cam 190 of the outer sleeve 155. The inner sleeve groove 175 and the outer sleeve groove 185 are designed in such a way in this case that, in a coupled state with the inner sleeve cam 180 and the outer sleeve cam 190, the return motion of the outer sleeve 155 is effectuated in response to the second actuation of the actuation device 125 and, subsequent thereto, the return motion of the inner sleeve 150.

The opening device 135 comprises an opening unit 192 which is designed for opening the blood vessel before the punching, in response to the forward motion of the implantation device 120. For this purpose, the opening device 135 according to this exemplary embodiment is coupled to the implantation device 120 and, in addition, is accommodated in the implantation device 120. The opening device 135 comprises an opening device cam 194 which is accommodated by an opening device groove 196 of the linear unit 165. The opening unit 192 comprises a barb which is designed for captively fixing a blood vessel section of the blood vessel to be punched, during the opening of the blood vessel.

Details which have already been described with reference to FIG. 1 are commented on again, more precisely, in the following.

As technology matures, machines will be implanted in the bodies of humans to an increasing extent, and so there is a need for a device which punches a hole into a blood vessel, which was referred to previously as a blood vessel, in a minimally invasive way and implants a wire mesh such as the implant device 105 into the blood vessel, the wire mesh holding this hole open. Such a device is the punching device 100 presented here. Cables can be routed out of the blood vessels or slid into the blood vessels, for example, through the hole punched by means of the punching device 100. One example of such a machine is the mechanical ventricular assist device (VAD). These machines carry out their function in the body. In order to ensure a power supply to these machines in the blood vessels, it will become necessary increasingly frequently in the future to route power cables or general supply cables through blood vessel walls.

The punching device 100 presented here is designed for punching—on the pulsating blood, vessel, in particular on the beating aorta, without clamping the aorta—a hole into the aorta and introducing an implant device 105, through which a supply cable can be routed. After the supply cable is routed through, the implantation is tightly sealed.

The clamping of the aorta can be advantageously dispensed with in this case, which has considerable advantages for the patient, since the clamping of blood vessels can lead to the formation of thrombi, for example. If these thrombi become detached and travel, for example, to a constriction in the brain, this can result in a cerebrovascular accident.

In addition, the patient advantageously does not need to be connected to a heart-lung machine during the punching of the blood vessel and implantation of the implant device 105 by means of the punching device 100. The heart-lung machine is an invasive method that surgeons like to avoid if at all possible.

In addition, when the punching device 100 presented here is utilized, for example, on the aorta, only a partial sternotomy is necessary. Devices for implanting bypasses at the aorta, in the case of which the aorta is punched and an anastomosis is established between the aorta and a vein, which had been previously removed, cannot be used for the application described. An anastomosis refers to a natural or artificial connection between blood vessels. These devices are too large and require a complete sternotomy. The approach presented here, however, takes place less invasively, i.e., only a partial sternotomy is necessary in the case of an application of the punching device 100 at the aorta.

As described above, the punching device 100 presented here makes it possible to carry out the described type of surgical procedures less invasively and with less risk. Due to the use of the punching device 100, it is not necessary to clamp the blood vessels or utilize a heart-lung machine. In addition, the operation can be carried out using a partial sternotomy. Given that there is no need to suture the blood vessels, the duration of the operation is reduced and the handling is simplified. Instead of cutting the blood vessel open, punching a hole, inserting a stent, and suturing in order to seal, the surgeon can simply turn the rotary knob 125 or, according to one alternative exemplary embodiment, press on the push-button.

The punching device 100 integrates, in short, the functions of punching the blood vessel, removing the punched-out tissue, and implanting an implant device 105 which holds the hole open with a defined inner diameter.

In this case, the punching device 100 is protected against slipping during the process. The implant device 105 seals toward the outside and, after the cable has been routed through, it also seals toward the inside. The punching device 100 is used only one time. The implant device 105 remains implanted in the body for the same length of time as the cable which is routed through the hole that is produced. The punching device 100 functions purely mechanically. The required introduction of force takes place either by reloading the spring 170 or, according to one alternative exemplary embodiment, by means of the muscular force of the surgeon.

Represented here is a cross-section of a side view of the punching device 100 in the starting state with only one housing half of the housing 130. In one operating step, the punching device 100 can punch a hole into the blood vessel, remove the punched-out tissue, and implant a wire mesh which seals toward the outside. Initially, the punching device 100 is pressed onto the blood vessel to be worked on. A device, which is not described in further detail and which can be coupled, for example, to the punching device 100, prevents the punching device 100 from slipping. A next operating step is disengaging the securing mechanism. This takes place via an axial motion of a securing button of the punching device 100. Next, the rotary knob 125 is rotated through one to two revolutions in all. As a result, the linear unit 165 is rotated, on the surface of which guide grooves in the form of the inner sleeve groove 175 presented here, the outer sleeve groove 185, and the opening device groove 196 extend. The linear unit 165 can also be referred to as a guide shaft. These guide grooves make it possible for different tools in the form of the inner sleeve 150 and the outer sleeve 155 of the implantation device 120 and the opening device 135 to move relative to one another using only one operating element. The tools required for implementing the desired application each comprise a pin in the form of the inner sleeve cam 180, the outer sleeve cam 190, and the opening device cam 194, for example made of metal, each extending in a groove in the linear unit 165 provided separately therefor. The aforementioned securing mechanism also functions in this way. It also includes a securing pin which extends in a securing groove. Before the securing mechanism of the punching device 100 is disengaged, the securing pin is located in a small recess on the linear unit 165, whereby the rotary motion of the linear unit 165 is blocked. The individual tools are guided by guide rails which are disposed on the inner housing wall of the housing halves of the housing 130. The guide rails are disposed close to a plane of the largest force transmission in this case. This means that the guide rails of the inner sleeve 150, the outer sleeve 155, and the opening device 135 lie close to the linear unit 165.

The first motion that is implemented according to this exemplary embodiment by rotating the rotary knob 125, is an abrupt, axial forward motion of the punching tool by 5 mm to 15 mm. The punching tool is simultaneously a punch and the implant device 105. It is a wire mesh that punches a hole into the blood vessel and is subsequently directly implanted. The compressed state of the wire mesh is more clearly apparent in FIG. 2. The outer sleeve 155 is positioned around the wire mesh during the punching process so that the wire mesh is provided with the stiffness required for punching. The outer sleeve 155 also prevents an unwanted, premature expansion of the wire mesh. Punching is carried out during the forward motion. An opening unit 192 comprising a barb, which is located within the punching wire mesh, move along with the implant device 105 into the blood vessel. After the punching process, the opening unit 192, including the barb and the punched-out tissue, is withdrawn and the wire mesh expands. The expansion of the wire mesh takes place by means of the retraction, i.e., the return motion, of the outer sleeve 155. With the aid of the acting radial force, the mesh is affixed on the blood vessel and simultaneously seals toward the outside. The abrupt opening motion of the linear unit 165 is implemented by the spring 170 which can be a compression spring and is located on the linear unit 165. The spring 170 was preloaded during installation by means of the plug-and-socket connection, i.e., the bayonet lock in this case. The bayonet lock is opened during the rotation of the rotary element 160 and the spring 170 is relaxed. The entire linear unit 165 moves axially along with the different tools in the form of the opening device 135, the inner sleeve 150 comprising the implant device 105, and the outer sleeve 150 by 5 mm to 12 mm. A hole has now been punched into the blood vessel and the wire mesh has been simultaneously implanted. The linear unit 165 is now rotated further. As a result, the two sleeves 150, 155, which are necessary for the expansion of the wire mesh, are retracted and the punching device 100 can be removed from the blood vessel. The two sleeves 150, 155 can be moved relative to each other. The outer sleeve 155 is retracted first, and so the wire mesh expands. Next, the inner sleeve 150, on which the wire mesh was located before the expansion, is retracted. A wire mesh which seals toward the outside is now located in the punched hole of the blood vessel, through which a supply cable can be routed. The mesh seals toward the inside only once the intended cable has been routed through. The aforementioned seal is not part of this approach, however. According to one alternative exemplary embodiment, the implant device 105 is tightly sealed without the cable passage. According to one alternative exemplary embodiment, the implant device 105 comprises a sealing unit which seals the hole during the implantation. Given that the implant device 105 is designed for deforming itself, the implant device 105 advantageously does not need to be deformed, for example, bent, by an external application of force during implantation.

The housing 130 of the punching device 100 consists of two housing halves which are connected to each other. Only one housing half is represented here, for the sake of clarity. Apart from the connection mechanism, the two housing halves are designed to be axially symmetrical with respect to each other.

The rotary knob can be replaced by the push-button when a preloaded torsion spring is relaxed by way of the actuation of the push-button.

This torsion spring then rotates the linear unit 165 at a previously calculated speed. Alternatively to the manual operation, the push-button can also be operated using a cordless screwdriver, which was designed especially for surgery, or using a screwdriver without a rechargeable battery.

Merely by way of example, the securing button has a length of 25 mm and a width of 10 mm, a securing-pin diameter is 3 mm, all other pins/cams 180, 190, 194 have a diameter of 3 mm, and the punching implant device 105 has an outer diameter of 3 mm to 7 mm and a length of 20 mm. Possible dimensions of the housing 130 of the punching device 100 are 212 mm×40 mm×28 mm (L×H×W). The rotary knob has a diameter of 40 mm to 50 mm, the linear unit 165 has a maximum diameter of 20 mm and a length (without the rotary knob) of 190 mm. The spring 170 has a length of 20 mm in the tensioned state 145 and a length of 40 mm in the relaxed state.

By way of example, the spring 170 is made of spring steel, the pins/cams 180, 190, 194 and the opening unit 192 comprising the barb is made of stainless steel, the implant device 105 is made of a wire mesh made of Nitinol, and a seal that is used is made of silicone. The further elements can be made of a biocompatible plastic, such as ABS M30i or the like.

Possible methods for producing the plastic parts include, in this case, by way of example, an injection molding process or 3D printing, for example, an FDM process.

Figure 2:
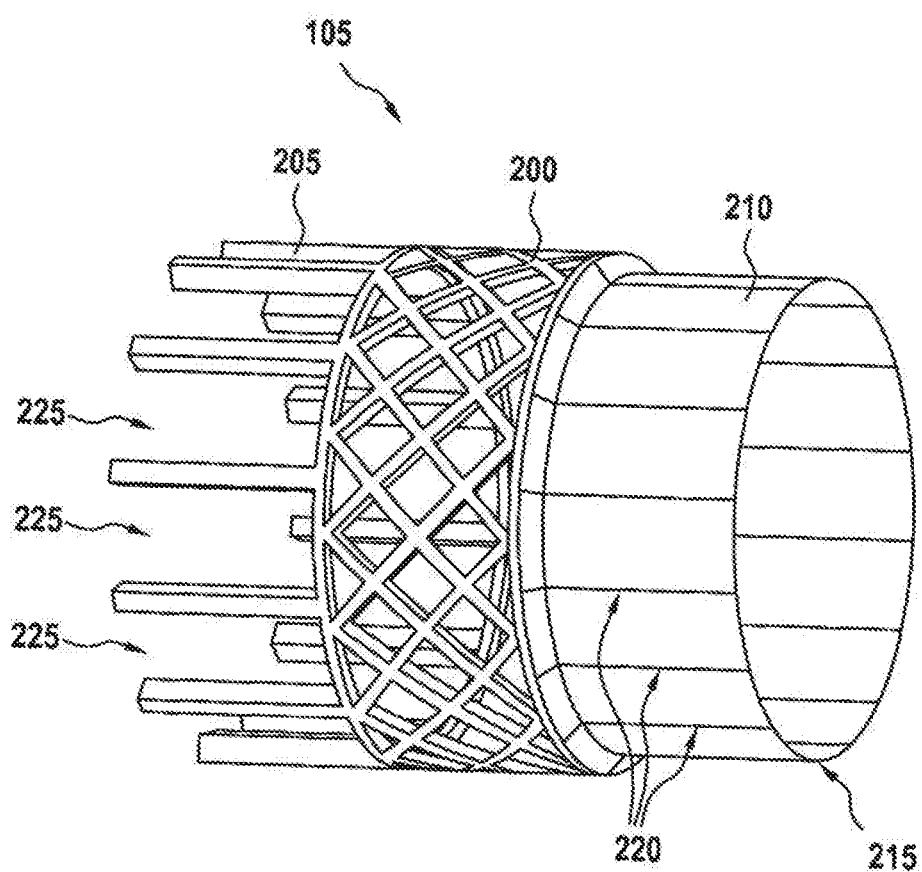
FIG. 2 shows a perspective side view of an implant device in an implantation device according to one exemplary embodiment.

FIG. 2 shows a perspective side view of an implant device 105 in an implantation device according to one exemplary embodiment.

The implant device 105 is disposed in the implantation device in the compressed state in which the implant device 105, according to this exemplary embodiment, is tubular overall. According to this exemplary embodiment, the implant device 105 comprises, in a central region, a wire mesh ring 200 from which a clamping section 205 extends in one direction and a punching section 210 extends in an opposite direction. The punching section 210, in a state disposed in the punching device 100, faces the outlet opening and comprises a cutting edge 215 on a free end. The cutting edge 215 can also be referred to as a blade and is designed for punching the blood vessel by means of the forward motion. According to this exemplary embodiment, the punching section 210 comprises a plurality of longitudinal slots 220 and the clamping section 205 comprises a plurality of recesses 225. The longitudinal slots 220 and the recesses 225 allow for a deformation of the clamping section 205 and the punching section 210 during implantation of the implant device 105. The implant device 105 is represented in a deformed, implanted state in FIG. 4.

Figure 3:
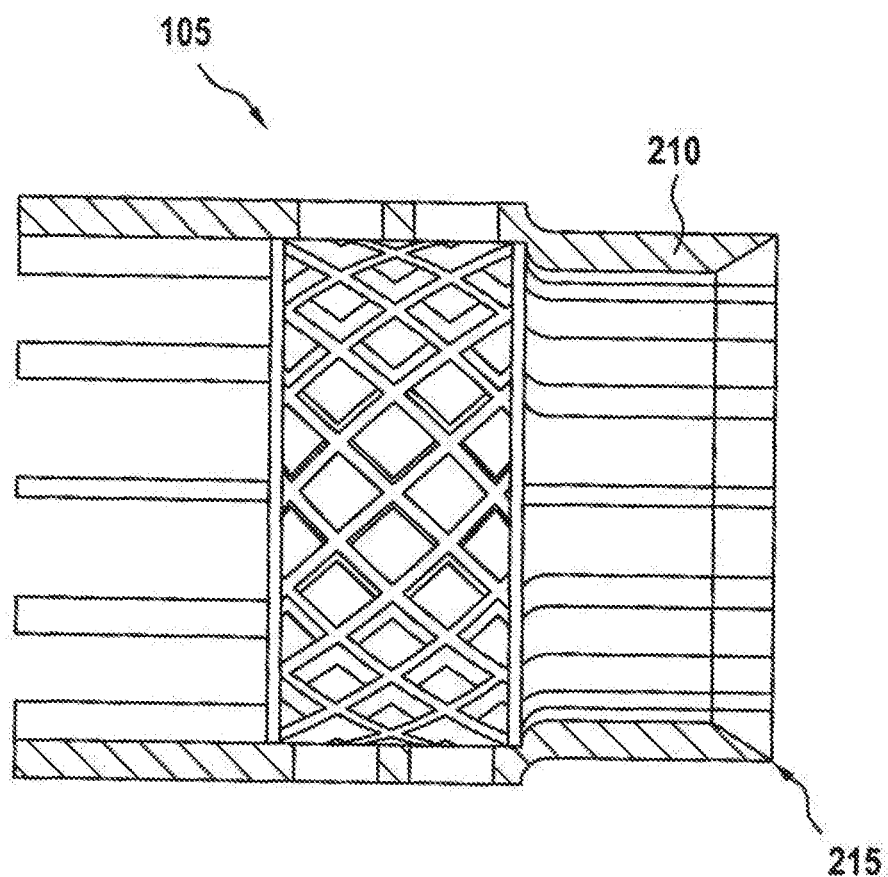
FIG. 3 shows a cross-section of a side view of an implant device in an implantation device according to one exemplary embodiment.

FIG. 3 shows a cross-section of a side view of an implant device 105 in an implantation device according to one exemplary embodiment. This can be the implant device 105 described with reference to FIG. 2.

The wire mesh is designed to be slanted and to have a sharp edge in the region of the cutting edge 215 so that punching is possible.

Figure 4:
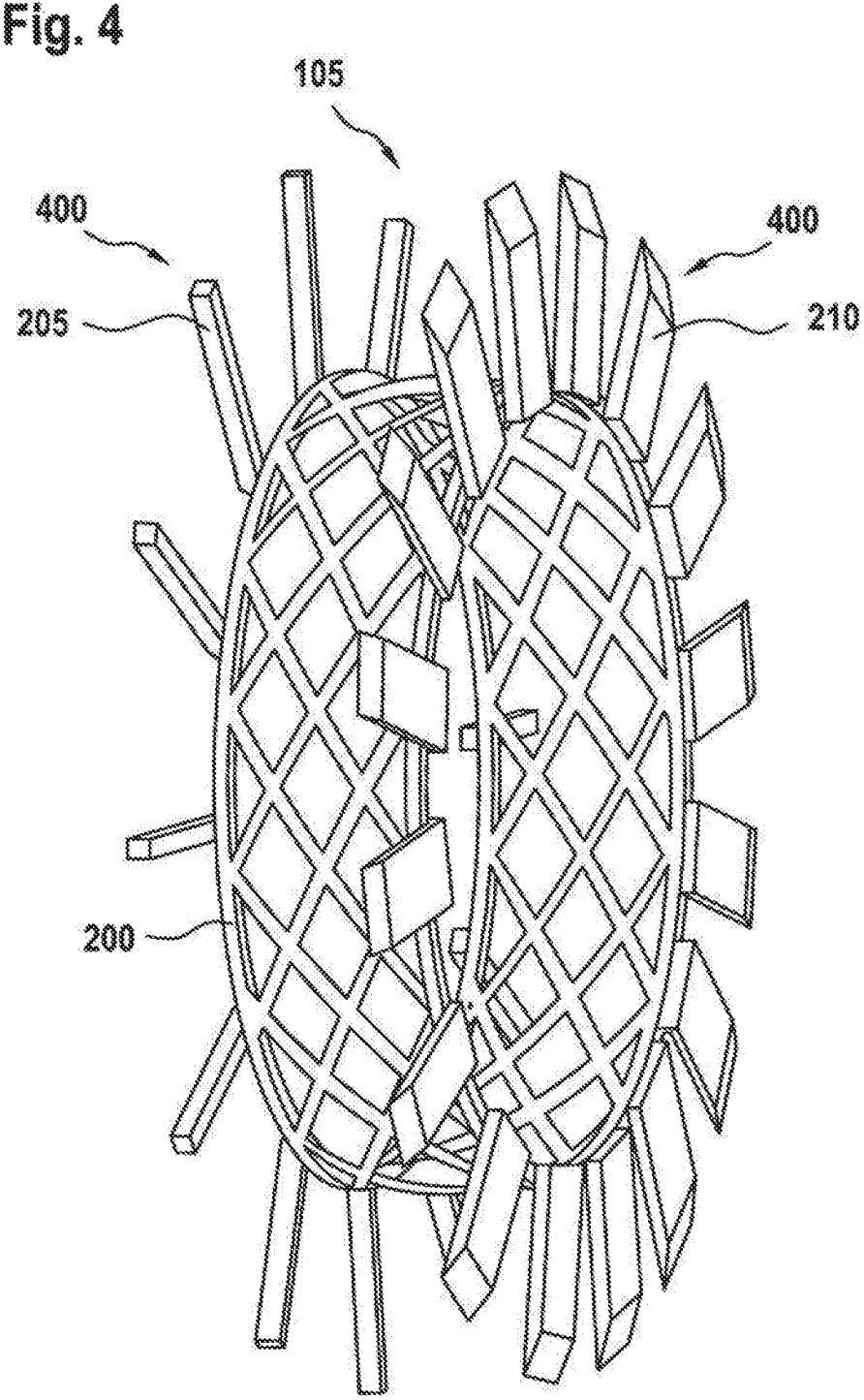
FIG. 4 shows a perspective side view of an implant device in an implanted state according to one exemplary embodiment.

FIG. 4 shows a perspective side view of an implant device 105 in an implanted state 400 according to one exemplary embodiment. This can be an implant device 105 described with reference to the preceding figures.

The clamping section 205 and the punching section 210 are shown deformed in the implanted state 400 after the return motion of at least the outer sleeve of the implantation device according to this exemplary embodiment. The clamping section 205 and the punching section 210 have deployed radially outwardly in this case by 90° around the wire mesh ring 200 according to this exemplary embodiment and are therefore each disposed perpendicular to the wire mesh ring 200. In the implanted state 400, the clamping section 205 and the punching section 210 are designed for fixedly clamping the implant device 105 in the blood vessel around the punched hole. The wire mesh ring 200 is deformed in an expanded state.

Figure 5:
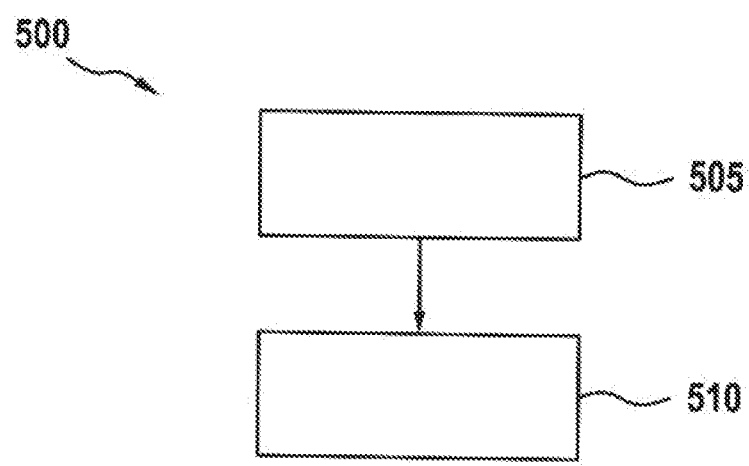
FIG. 5 shows a flow chart of a method for punching a lumen and implanting an implant device according to one exemplary embodiment.

FIG. 5 shows a flow chart of a method 500 for punching a lumen and implanting an implant device according to one exemplary embodiment. This can be a method 500 that can be implemented by the punching device described with reference to FIG. 1.

In a step 505 of bringing about, an opened state of a closure device is brought about for the purpose of releasing a restoring force for effectuating a forward motion of an implantation device coupled to the closure device, in order to punch the blood vessel by means of the the implant device coupled to the implantation device, wherein the opened state of the closure device is brought about by means of at least one actuation of an actuation device coupled to the closure device. In a step 510 of execution, a return motion of the implantation device is executed in order to effectuate an implantation of the implant device, which is coupled to the implantation device, into the punched blood vessel, wherein the return motion of the implantation device is executed by means of the at least one actuation of the actuation device.

If one exemplary embodiment has an "and/or" operation between a first feature and a second feature, this should be read to mean that the exemplary embodiment according to one exemplary embodiment comprises both the first feature and the second feature and, according to another exemplary embodiment, comprises either only the first feature or only the second feature.

The invention claimed is:

1. A punching device for punching a lumen, comprising:
an implant device including a cutting edge configured to punch a hole in the lumen, the implant device configured to be implanted into the lumen through the hole;
an implantation device coupled to the implant device, the implantation device configured to punch the implant device toward the lumen to cut the hole with the cutting edge and to position the implant device at least partially within hole by way of a forward motion, and the implantation device further configured to effectuate the implantation of the implant device into the after the lumen has been punched lumen by way of a return motion of at least one part of the implantation device;
a closure device coupled at least to the implantation device and including a spring, in a closed state of the closure device the spring is configured to generate a restoring force, and in an opened state of the closure device the closure device releases the restoring force, wherein the released restoring force is configured to effectuate the forward motion of the implantation device in order to punch the hole in the lumen with the cutting edge; and
an actuation device coupled to the closure device, wherein the actuation device is configured to bring about the opened state of the closure device and to effectuate the return motion of the implantation device in response to at least one actuation.

2. The punching device according to claim 1, wherein the implantation device comprises at least one inner sleeve configured to guide the implant device and an outer sleeve configured to surround the implant device, and wherein the outer sleeve is further configured to surround the inner sleeve in an at least partially linearly movable manner.

3. The punching device according to claim 2, wherein the outer sleeve is configured to carry out the return motion in order to effectuate the implantation of the implant device into the lumen after the lumen has been punched.

4. The punching device according to claim 1, further comprising:
an opening device coupled to the implantation device, wherein the hole in the lumen is a first hole, and
wherein the opening device comprises at least one opening unit that is configured to open a second hole in the lumen before the cutting edge punches the first hole in the lumen in response to the forward motion.

5. The punching device according to claim 4, wherein:
the opening unit comprises a barb configured to captively fix a lumen section of the lumen, which is to be punched out, during the punching of the first hole in the lumen by the cutting edge, and
the barb is further configured to remove the lumen section from the lumen during the return motion of the implantation device.

6. The punching device according to claim 4, wherein the opening device is disposed at least partially in one or more of the implantation device and the implant device.

7. The punching device according to claim 1, wherein the implant device comprises a mesh having shape memory.

8. The punching device according to claim 1, wherein:
the closure device comprises a bayonet lock including a rotatable rotary element and a rotatable and linearly movable linear unit, and
the spring is loaded in a closed state of the bayonet lock in order to generate the restoring force.

9. The punching device according to claim 8, wherein the bayonet lock is configured to be transferred from the closed state into the opened state by a rotation of the rotary element, and wherein the rotatable and linearly movable linear unit is configured such that, when the bayonet lock is transferred into the opened state, the rotatable and linearly movable linear unit executes a linear opening motion in the direction of an outlet opening of the punching device in order to effectuate the forward motion of the implantation device coupled to the rotatable and linearly movable linear unit.

10. The punching device according to claim 8, wherein, in order to couple the closure device to the implantation device, at least one sleeve of the implantation device comprises at least one pin to be accommodated in at least one guide groove of the rotatable and linearly movable linear unit and/or the rotatable and linearly movable linear unit comprises at least the guide groove for accommodating the pin of the sleeve, and wherein the guide groove and the pin are configured such that, in the coupled state, the guide groove and the pin effectuate the return motion of the implantation device in response to the actuation of the actuation device after the lumen has been punched.

11. The punching device according to claim 1, wherein the actuation device comprises at least one rotary knob configured to effectuate the at least one actuation of the actuation device in response to a rotary actuation.

12. The punching device according to claim 1, wherein the actuation device comprises at least one push-button configured to effectuate the at least one actuation of the actuation device in response to a push actuation.

13. The punching device according to claim 1, wherein at least the implant device and the implantation device are disposed on one axis.

* * * * *